(12) United States Patent
Wang

(10) Patent No.: US 9,474,587 B2
(45) Date of Patent: Oct. 25, 2016

(54) DENTURE-FIXING ATTACHMENT HAVING FREELY ADJUSTABLE ANGLE AND POSITION

(71) Applicant: Je Won Wang, Daejeon (KR)

(72) Inventor: Je Won Wang, Daejeon (KR)

(*) Notice: Subject to any disclaimer, the term of this patent is extended or adjusted under 35 U.S.C. 154(b) by 61 days.

(21) Appl. No.: 14/384,916

(22) PCT Filed: Mar. 22, 2013

(86) PCT No.: PCT/KR2013/002381
§ 371 (c)(1),
(2) Date: Sep. 12, 2014

(87) PCT Pub. No.: WO2013/151258
PCT Pub. Date: Oct. 10, 2013

(65) Prior Publication Data
US 2015/0010884 A1 Jan. 8, 2015

(30) Foreign Application Priority Data

Apr. 4, 2012 (KR) .................. 20-2012-0002752 U

(51) Int. Cl.
*A61C 8/00* (2006.01)

(52) U.S. Cl.
CPC ........... *A61C 8/0053* (2013.01); *A61C 8/0048* (2013.01); *A61C 8/0069* (2013.01)

(58) Field of Classification Search
CPC A61C 8/0053; A61C 8/0074; A61C 8/0054; A61C 8/0089; A61C 8/006; A61C 8/0057; A61C 8/0048; A61C 8/0069
USPC ................ 433/172, 173, 174, 175, 176, 191
See application file for complete search history.

(56) References Cited

U.S. PATENT DOCUMENTS

| | | | | |
|---|---|---|---|---|
| 4,713,004 A | * | 12/1987 | Linkow | A61C 8/0018 433/174 |
| 4,793,808 A | * | 12/1988 | Kirsch | A61C 8/0018 433/173 |
| 4,832,601 A | * | 5/1989 | Linden | A61C 8/005 433/173 |
| 4,842,518 A | * | 6/1989 | Linkow | A61C 8/0018 433/174 |
| 4,932,868 A | * | 6/1990 | Linkow | A61C 8/0018 433/174 |
| 4,934,935 A | * | 6/1990 | Edwards | A61C 8/0022 433/173 |
| 5,007,835 A | * | 4/1991 | Valen | A61C 8/0022 433/174 |
| 5,073,110 A | * | 12/1991 | Barbone | A61C 8/0001 433/173 |
| 5,178,539 A | * | 1/1993 | Peltier | A61C 8/005 433/173 |
| 5,194,000 A | * | 3/1993 | Dury | A61C 8/0018 433/173 |

(Continued)

FOREIGN PATENT DOCUMENTS

| | | |
|---|---|---|
| JP | 2001-170081 A | 6/2001 |
| JP | 2002-093481 | 3/2008 |

(Continued)

*Primary Examiner* — Nicholas Lucchesi
(74) *Attorney, Agent, or Firm* — Novick, Kim & Lee, PLLC; Jae Youn Kim

(57) ABSTRACT

Disclosed is a denture-fixing attachment freely adjustable in angle and position and including a rotation guide member installed at the center of the denture-fixing attachment, having a lower portion to be inserted into a fixture groove of a fixture, a thread being formed at a rim of the fixture groove, so that the rotation guide member may be coupled with the fixture having the fixture groove, a rotation guide member angle restriction cover positioned on the rotation guide member and provided therein with a through hole, and a ball joint having a ball joint lower portion placed in a rotation guide member inside provided in a ball joint angle restriction cover.

5 Claims, 7 Drawing Sheets

(56) References Cited

U.S. PATENT DOCUMENTS

| | | | | |
|---|---|---|---|---|
| 5,195,891 A * | 3/1993 | Sulc | | A61C 8/005 433/173 |
| 5,516,288 A * | 5/1996 | Sichler | | A61C 8/0001 433/173 |
| 5,564,922 A * | 10/1996 | Rosa | | A61C 8/005 433/173 |
| 5,890,902 A * | 4/1999 | Sapian | | A61C 8/0048 433/173 |
| 7,695,498 B2 * | 4/2010 | Ritland | | A61B 17/7007 606/264 |
| 7,959,439 B2 | 6/2011 | Bulloch et al. | | |
| 8,651,866 B2 * | 2/2014 | Bulard | | A61C 8/005 433/174 |
| 2004/0078040 A1 * | 4/2004 | Feijtel | | A61C 13/275 433/173 |
| 2007/0016200 A1 * | 1/2007 | Jackson | | A61B 17/7005 623/17.16 |
| 2009/0246733 A1 * | 10/2009 | Auderset | | A61C 8/005 433/173 |
| 2010/0209874 A1 * | 8/2010 | Auderset | | A61C 13/275 433/174 |
| 2011/0189635 A1 * | 8/2011 | Lauridsen | | A61C 8/0053 433/174 |
| 2014/0017631 A1 * | 1/2014 | Benzon | | A61C 8/0053 433/173 |
| 2014/0065574 A1 * | 3/2014 | Benzon | | A61C 8/0053 433/173 |
| 2014/0081333 A1 * | 3/2014 | Jackson | | A61B 17/7031 606/257 |
| 2014/0154643 A1 * | 6/2014 | Benzon | | A61C 8/0053 433/173 |
| 2014/0162212 A1 * | 6/2014 | Mullaly | | A61C 8/0053 433/173 |
| 2014/0170597 A1 * | 6/2014 | Honig | | A61C 8/0053 433/173 |
| 2014/0178837 A1 * | 6/2014 | Benzon | | A61C 8/0053 433/173 |
| 2014/0178838 A1 * | 6/2014 | McBride | | A61C 8/0053 433/173 |

FOREIGN PATENT DOCUMENTS

| | | |
|---|---|---|
| KR | 10-2007-0112075 A | 11/2007 |
| KR | 10-2009-0080572 A | 7/2009 |
| KR | 10-0925766 B1 | 11/2009 |
| KR | 10-1042372 B1 | 6/2011 |

\* cited by examiner (3A)   (3B)

(5A)

(5B)

DENTURE-FIXING ATTACHMENT HAVING FREELY ADJUSTABLE ANGLE AND POSITION

TECHNICAL FIELD

The present invention relates to a denture-fixing attachment freely adjustable in angle and position, which can be used to fix dentures after an implant treatment has been performed in the dentist.

BACKGROUND ART

Conventionally, when a tooth is pulled out, a false tooth is put in place of the pulled-out tooth or a dental bridge treatment, in which surrounding teeth are employed as pillars and a crown is positioned in place of the pulled-out tooth, is performed. However, the treatment causes various problems that false teeth or artificial teeth resulting from the bridge treatment are weak in chewing foods and exert a malicious influence on surrounding teeth.

Accordingly, as one treatment of an advanced dental medical technology, an implant treatment is introduced. According to the implant treatment, an artificial tooth root is formed in an alveolar bone, and an artificial tooth produced significantly similar to a real tooth is coupled with the artificial tooth root, so that a patient obtains an effect of using the real tooth.

According to the implant treatment procedure, an implant groove is formed by using a tool, such as a drill, to implant a fixture in an alveolar bone having no tooth, and a tapping work is selectively performed to securely implant the fixture into the implant groove. Then, after implanting the fixture into the implant groove, a cover screw is coupled with the fixture to prevent foreign matters from being infiltrated into the fixture and covered on a gum, and the gum is sutured, thereby finishing a primary procedure.

Thereafter, according to a secondary procedure, after about three or six months have been elapsed, the sutured gum is incised again, and the cover screw is removed from the fixture. Then, a heeling abutment is selected by taking into consideration to an abutment to be coupled to the fixture and coupled with the fixture, and the gum is sutured in such a manner that the interval between neighboring teeth is not spread.

The healing abutment cleanly forms a gum on the fixture before the abutment is coupled to the fixture. After about two or three weeks have been elapsed from a time at which the healing abutment is coupled, the healing abutment is removed from the fixture and the abutment is coupled to the fixture. Accordingly, an artificial tooth formed through a mold is coupled onto the abutment, thereby completing the implant treatment.

As described above, a scheme of performing the secondary procedure after the fixture is buried in the gum and an outer portion of the fixture is completely covered with the gum is called a submerged type procedure.

In the above submerged type of the implant treatment process, the fixture implanted in the alveolar bone serves as a tooth root, and the abutment is a connection component to integrate the abutment with the artificial tooth.

In particular, the fixture and the abutment constitute an implant structure to securely fix the artificial tooth to a right position. The implant structure is generally formed of titanium physically/chemically representing superior strength.

In general, although the implant originally refers to a substitute to recover a missed portion of a human body, the implant refers to putting an artificial tooth in a gum in the dentist. After a tooth root made of titanium having no rejection to a human body is implanted into the alveolar bone that a tooth is pulled out so that the titanium tooth root may be substituted for a missed tooth root (root), the artificial tooth is fixed to the tooth root so that the function of the tooth can be recovered.

Although a typical prosthetic appliance or a typical false tooth damages surrounding teeth or bones according to the elapse of the time, an implanted tooth does not damage a surrounding tooth structure, and performs the function of an original tooth in the same shape as that of the original tooth. In addition, the implanted tooth is not decayed, so that the implanted tooth can be semipermanently used.

In Korean Registration No. 1009257660000 (published on Nov. 2, 2009), a metallic member or "abutment" is received in a dental implant, milled, or prepped to receive a dental prosthetic device. The metallic member has a concave part extending upward from a bottom in an axial direction, and the concave part is fitted around an O-ball or an O-ring receiver abutment of the dental implant. The abutment including a coupling protrusion is provided, the coupling protrusion is placed in a coupling groove formed in an upper portion of the fixture, the abutment is coupled to the fixture by using the screw, a prosthesis including a screw hole is provided, and dental cement is interposed between the abutment and the prosthesis to bond the prosthesis to the abutment, thereby constituting a prosthesis mounting device and assembly to be disclosed.

In addition, Korean Patent Registration No. 1009257660000 (issued on Nov. 2, 2009) discloses an integral type implant provided at a lower portion thereof with a screw part having a lower portion provided at an outer portion thereof with a thread so that the screw part may be rotated about one axis and implanted into a dentary bone, and provided at an upper portion thereof with an abutment that may be formed integrally with the screw part, buried in a gum covering the dentary bone, and covered with a cap. The abutment includes a gingival level part making contact with the gum and a protrusion provided at an upper portion of the gingival level part and detachably coupled to the cap. The protrusion has a coupling groove extending downward of a top surface thereof, and the coupling groove has a sectional shape that may be engaged with a driver used to rotate the implant.

Korean Unexamined Patent Application No. 10-2007-0112075 discloses a detachable type abutment for dental implant that is fixed to a fixture implanted into an alveolar bone to support a dental prosthesis. The abutment includes a fixing member fixed to the fixture, an upper member fixed to the dental prosthesis, and a coupling structure to separately couple the upper member to the lower member.

Prior arts are listed as follows.
(Patent Document 0001) 1. Korean Patent Registration No. 1009257660000 (issued on Nov. 2, 2009)
(Patent Document 0002) 2. Korean Patent Registration No. 1010423720000 (issued on Jun. 10, 2011)
(Patent Document 0003) 3. Korean Unexamined Patent Application No. 10-2007-0112075.

DISCLOSURE

Technical Problem

An object of the present invention is to dissolve inconveniences of conventional abutment technologies for fixing dentures in which a reoperation is performed so that the fixtures are implanted in parallel to each other or additional parts are used as an abutment for fixing a denture cannot be coupled with the denture when several fixtures implanted into a patient are not arranged in parallel to each other.

Technical Solution

In order to accomplish the above objects, there is provided a denture-fixing attachment freely adjustable in angle and position and including a rotation guide member inserted into a fixture groove (11) of a fixture, a ball joint angle restriction cover positioned on the rotation guide member, and a ball joint interposed between the rotation guide member and the ball joint angle restriction cover.

Advantageous Effects

As described above, according to the present invention, when the fixture implanted in an inclination direction is coupled with the denture, the denture can be coupled with the fixture without additional parts. Even if the fixture has an inclination angle in the implant treatment, the ball joint compensates for the inclination angle of the fixture for the purpose of the implant treatment. Accordingly, the implant treatment can be comfortably and easily provided for a patient or a doctor. In other words, the implant treatment can be performed without an additional surgical operation, such as marrow transplantation. The problem related to the angle adjustment can be solved, and the economical problem of the implant treatment can be solved or the treatment time of the implant treatment can be reduced through the simple coupling scheme of parts. The distress of the patient and the economical burden of the patient can be reduced and the treatment time of an operator (doctor) can be reduced. Since a chewing pressure is not directly transferred to the fixture in use, the lifespan of the fixture can be increased.

BEST MODE

Mode for Invention

Figure 1:
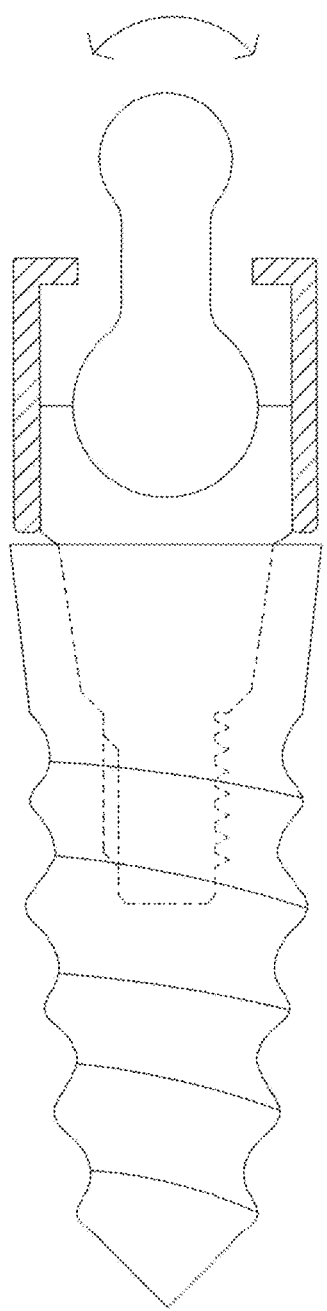
FIG. 1 is a perspective view showing the whole structure of a denture-fixing attachment freely adjustable in angle and position according to the present invention.

In order to accomplish the above objectives, the present invention provides a denture-fixing attachment freely adjustable in angle and position and including a rotation guide member 2 installed at the center of the denture-fixing attachment, having a lower portion to be inserted into a fixture groove 11 of a fixture 1 so that the rotation guide member 2 may be coupled with the fixture 1 having the fixture groove 11, a ball joint angle restriction cover 3 positioned on the rotation guide member 2 and provided therein with a through hole, and a ball joint 5 having a ball joint lower portion 51 placed in a rotation guide member inside 32 provided in the ball joint angle restriction cover 3.

Figure 2:
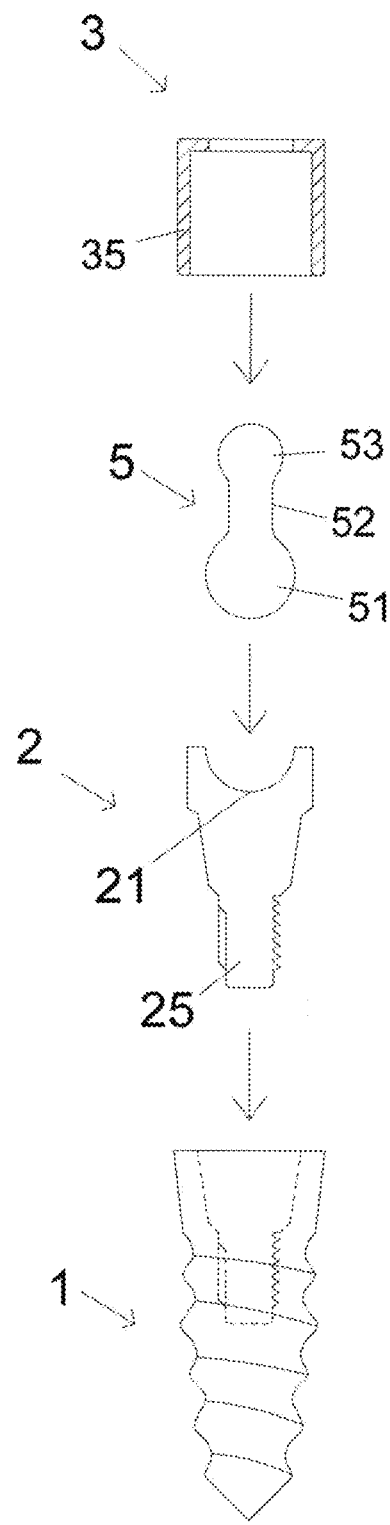
FIG. 2 is an exploded perspective view showing the denture-fixing attachment freely adjustable in angle and position according to the present invention.
Figure 3:
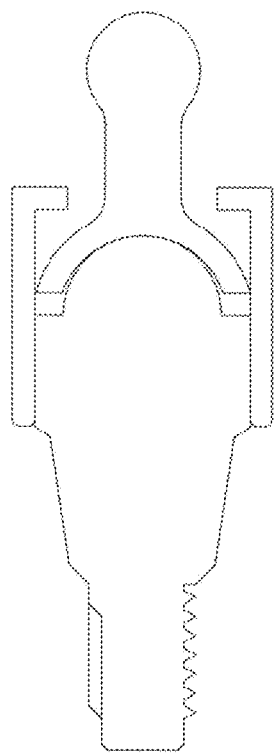
FIG. 3 shows other examples of the denture-fixing attachment freely adjustable in angle and position according to the present invention.
Figure 3:
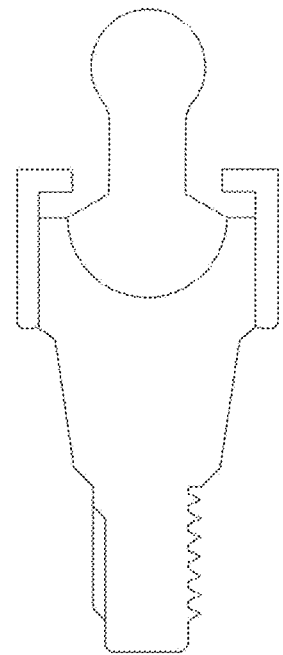

As shown in FIGS. 1 to 3, the rotation guide member 2 according to the present invention is coupled with the ball joint angle restriction cover 3 at an upper portion thereof.

A lower portion of the ball joint 5 is interposed between the rotation guide member 2 and the ball joint angle restriction cover 3, and an intermediate portion and an upper portion of the ball joint 5 protrude upward through the through hole formed through the center of the ball joint angle restriction cover 3.

A ball joint lower portion 51 of the ball joint 5, in which the ball joint 5 has the shape of a tumbling doll, and the ball joint lower portion 51 has the shape of a ball, is positioned in a rotation guide member upper groove 21 recessed in the shape of a half-moon at the upper portion of the rotation guide member 2.

As shown in FIG. 2, a ball joint upper portion 53, which has the shape of a ball, and a ball joint intermediate portion 52 of the ball joint 5 protrude upward of the ball joint angle restriction cover 3 by inserting the ball-shaped ball joint upper portion 53 and the ball joint intermediate portion 52 of the ball joint 5 from a lower portion to an upper portion of the through hole vertically formed through the center of the ball joint angle restriction cover 3. A rotation guide member lateral side (not shown) provided at an outer portion of the rotation guide member 2 is coupled with a ball joint angle restriction cover inside (not shown) of the ball joint angle restriction cover 3.

The rotation guide member lateral side may be coupled with the ball joint angle restriction cover inside by at least one of an adhesive agent, a screw, and a welding scheme using a laser.

Figure 6:
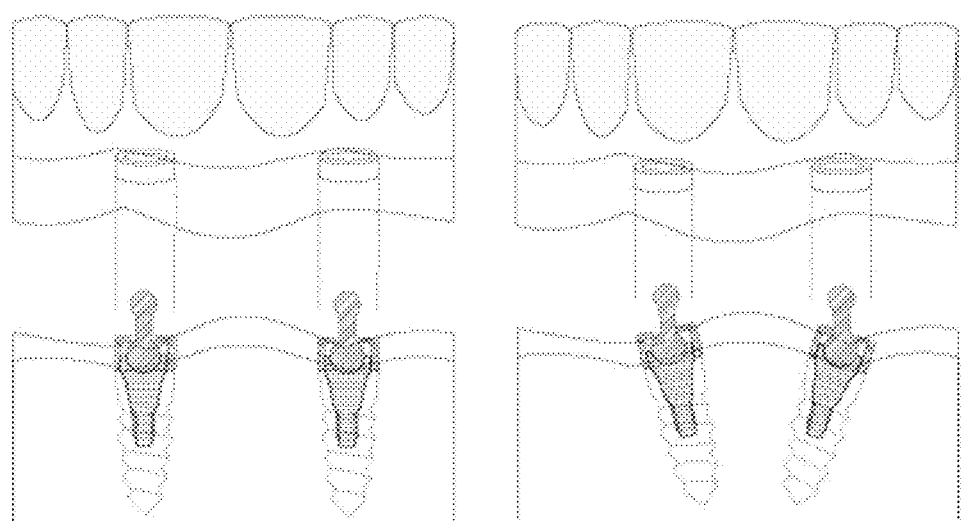
FIG. 6 shows a treatment state of the denture-fixing attachment freely adjustable in angle and position according to the present invention.

After the rotation guide member lateral side has been coupled with the all joint angle restriction cover inside, the ball joint 5 is rotated and fixed at a desirable angle as shown in FIGS. 3 and 6, an angle of the fixture 1, which is inclined, is corrected, and the ball-shaped ball joint upper portion 53 is coupled with dentures, thereby performing an implant treatment.

Figure 4:
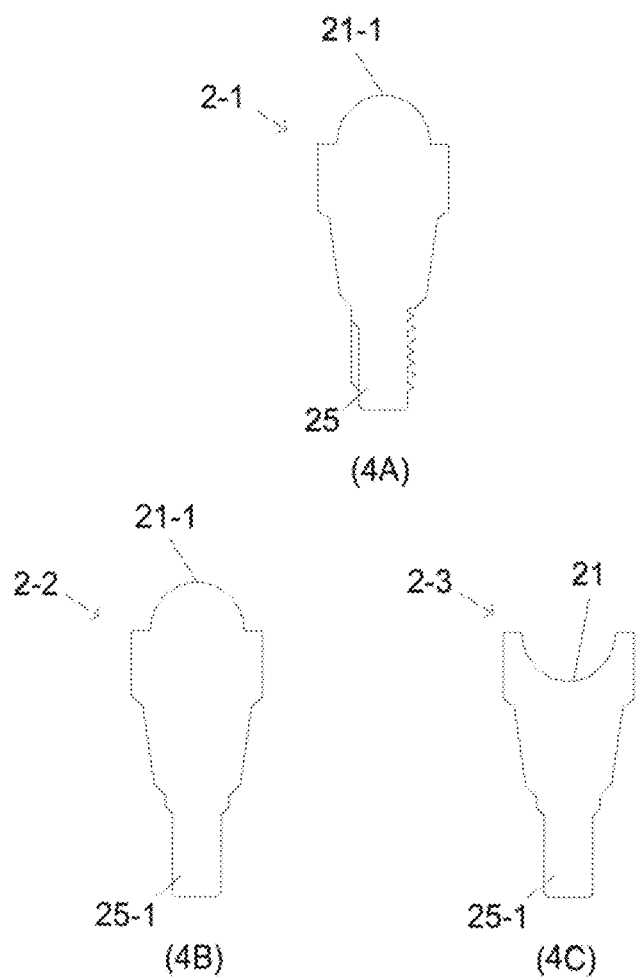
FIG. 4 shows other examples of the denture-fixing attachment freely adjustable in angle and position according to the present invention.

FIG. 4 shows another example of the rotation guide member 2.

The rotation guide member 2 shown in FIG. 4 is provided at the upper portion thereof with a protrusion instead of a protrusion, and a lower portion of the rotation guide member 2 has no a thread.

Figure 5:
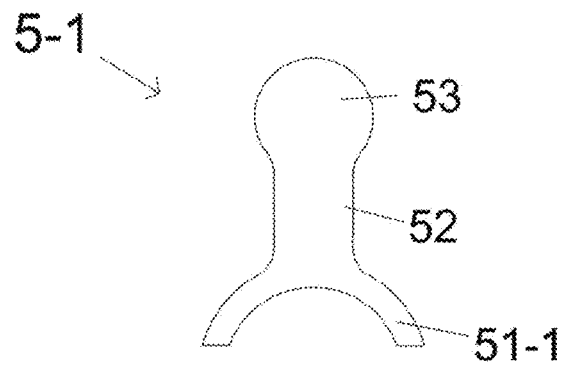
FIG. 5 shows other examples of a rotation guide member angle restriction cover according to the present invention.
Figure 5:
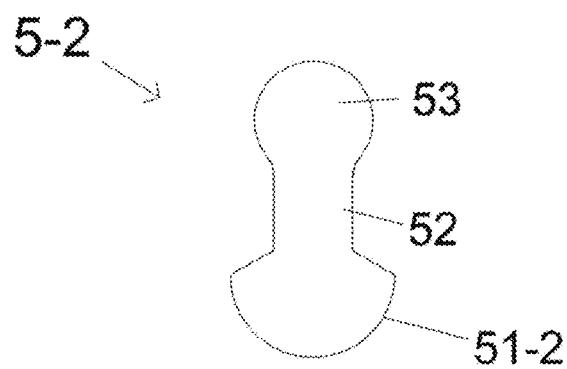

FIG. 5 shows another example of a ball joint.

A lower portion of the ball joint is modified corresponding to another example of the rotation guide member shown in FIG. 4.

FIG. 3 shows another example of the rotation guide member and another example of the ball joint as described above. FIG. 6 is an assembling view showing the implant state of the denture-fixing attachment freely adjustable in angle and position according to the present invention.

Hereinafter, the denture-fixing attachment freely adjustable in angle and position according to an embodiment of the present invention will be described in detail.

Embodiment

An implant groove is formed by a tool such as a drill to implant a fixture into an alveolar bone having no tooth, and a tapping work is selectively performed to securely implant the fixture into the implant groove. Then, after implanting the fixture into the implant groove, a rotation guide member lower portion 25 of the rotation guide member 2 is coupled with the fixture groove 11 of the fixture 1. Then, the ball joint lower portion 51 of the ball joint 5, in which the ball joint 5 has the shape of a tumbling doll, and the ball joint lower portion 51 has the shape of a ball, is positioned in the rotation guide member upper groove 21 recessed in the shape of a half-moon at the upper portion of the rotation guide member 2.

The ball joint angle restriction cover 3, which is vertically formed, is covered on the ball-shaped ball joint upper portion 53, which has a diameter smaller than that of the ball joint lower portion 51, and the ball joint intermediate portion 52 of the ball joint 5, so that the ball-shaped ball joint upper portion 53 and the ball joint intermediate portion 52 of the ball joint 5 protrude upward of the ball joint angle restriction cover 3.

In addition, the rotation guide member lateral side (not shown), which is positioned at the upper portion of the rotation guide member 2 and provided at an outer portion thereof with a thread, is coupled with the ball joint angle restriction cover inside (not shown) of the ball joint angle restriction cover 3 by the adhesive agent, the screw, or the welding scheme using the laser. Then, the ball joint 5 is rotated and fixed at a desirable angle as shown in FIG. 3, the angle of the fixture 1, which is inclined, is corrected, and the ball-shaped ball joint upper portion 53 is coupled with the dentures, thereby performing an implant treatment.

Hereinafter, the denture-fixing attachment freely adjustable in angle and position according to the present invention will be described in detail.

Figure 7:
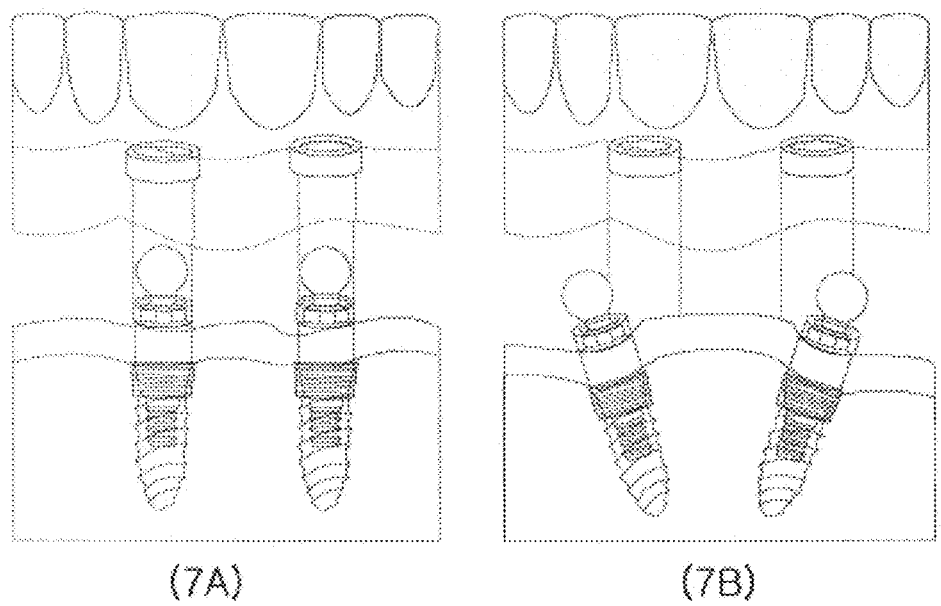
FIG. 7 shows a treatment state of the denture-fixing attachment according to the related art.

FIG. 1 is a view showing the whole structure of the denture-fixing attachment freely adjustable in angle and position according to the present invention, and FIG. 2 is an exploded perspective view showing the denture-fixing attachment freely adjustable in angle and position according to the present invention. FIG. 3 is a view showing another example of the denture-fixing attachment freely adjustable in angle and position according to the present invention. FIG. 4 is a view showing another example of the rotating guide member, and FIG. 6 is a view showing another example of the ball joint angle restriction cover according to the present invention. FIG. 7 shows an implant treatment state of the denture-fixing attachment freely adjustable in angle and position according to the present invention. FIG. 8 shows an implant treatment state of a denture-fixing attachment freely adjustable in angle and position according to the related art. In detail, the fixture 1, rotation guide members 2, 2-1, 2-2, and 2-3, the ball joint angle restriction cover 3, ball joints 5, 5-1, and 5-2, a fixture groove 11, a rotation guide member upper groove 21, a rotation guide member upper protrusion 21-1, a rotation guide member lateral side (not shown), rotation guide member lower portions 25 and 25-1, a ball joint angle restriction cover inside (not shown), a ball joint angle restriction cover lateral side 35, ball joint lower portions 51, 51-1, and 51-2, the ball joint intermediate portion 52, and the ball joint upper portion 53 are shown.

Regarding the structure of the denture-fixing attachment according to the related art, as shown in FIGS. 1 and 2, the denture-fixing attachment freely adjustable in angle and position according to the present invention includes the rotation guide member 2, 2-1, or 2-2 provided at the center of the denture-fixing attachment and having a lower portion inserted into the fixture groove 11 of the fixture 1 so that the rotation guide member 2, 2-1, or 2-2 may be coupled with the fixture 1 having the fixture groove 11, the ball joint angle restriction cover 3 positioned on the rotation guide member 2, 2-1, 2-2, or 2-3, having a space part therein, and provided at an upper portion thereof with a through hole, and the ball joint 5, 5-1, or 5-2 having the ball joint lower portion 51, 51-1, or 51-2 placed in a rotation guide member inside 31 provided in the ball joint angle restriction cover 3.

As shown in FIG. 2, the rotation guide member 2 includes the rotation guide member lower portion 25 provided therein with an inner space, provided at an upper portion thereof with a through hole, extending downward to be inserted into the fixture groove 11 and provided at an outer portion thereof with a thread, a rotation guide member lateral side (not shown) provided on the rotation guide member lower portion 25 and provided therein with a half-moon shaped groove, and a ball joint angle restriction cover lateral side 35 installed outside the lateral side of the rotation guide member 2.

The ball joint angle restriction cover 3 includes a ball joint angle restriction cover lateral side (not shown) that is positioned on the rotation guide member 2, coupled with the rotation guide member lateral side (not shown) provided at an outer upper portion of the rotation guide member 2, and allows the ball joint lower portion 51 having a ball shape to be placed in the ball joint angle restriction cover lateral side (not shown).

The ball joint 5 has the shape of a dumbbell and includes the ball joint lower portion 51 having the shape of the ball, the ball joint intermediate portion 52 installed at the upper portion of the ball joint lower portion 51, having a diameter smaller than that of the ball joint lower portion 51, and having the shape of a cylinder, and the ball joint upper portion 53 installed at the upper portion of the ball joint intermediate portion 52, having a diameter greater than that of the ball joint intermediate portion 52 and smaller than that of the ball joint lower portion 51, and having the shape of a ball.

FIG. 4 shows various examples of the rotation guide member 2 according to the present invention.

FIG. 4A shows the same structure as that of FIG. 2 except that the rotation guide member upper protrusion 21-1 is provided instead of the rotation guide member upper groove 21, and the details thereof will be described below.

The rotation guide member 2 includes the rotation guide member lower portion 25 extending downward to be inserted into the fixture groove 11 and provided at an outer portion thereof with a thread, the rotation guide member lateral side (not shown) positioned on the rotation guide member lower portion 25, and the rotation guide member upper protrusion 21-1 protruding in the shape of a half-moon at the upper portion of the rotation guide member 2.

FIG. 4B has the same structure as that of FIG. 4A except for the rotation guide member lower portion 25-1 having no tread, and the details thereof will be described below.

The rotation guide member 2 includes the rotation guide member lower portion 25 extending downward to be inserted into the fixture groove 11, the rotation guide member lateral side (not shown) positioned on the rotation guide member lower portion 25, and the rotation guide member upper groove 21-1 protruding in the shape of a half-moon at the upper portion of the rotation guide member 2.

FIG. 4C has the same structure as that of FIG. 2 except for the rotation guide member lower portion 25-1 having no tread, and the details thereof will be described below.

The rotation guide member 2 includes the rotation guide member lower portion 25 extending downward to be inserted into the fixture groove 11, the rotation guide member lateral side (not shown) provided on the rotation guide member lower portion 25, and the rotation guide member upper groove 21 recessed in the shape of a half-moon at the upper portion of the rotation guide member 2.

FIG. 5 shows another example of the ball joint.

The ball joint 5-1 shown in FIG. 5A has the shape of a dumbbell, and includes a ball joint lower portion 51-1 having a lower portion provided in the shape of a bow ( ), a ball joint intermediate portion 52 provided on the ball joint lower portion 51-1, having a diameter smaller than that of the ball joint lower portion 51-1 and having the shape of a cylinder, and a ball joint upper portion 53 provided on the ball joint intermediate portion 52, having a diameter greater than that of the ball joint intermediate portion 52 and smaller than that of the ball joint lower portion 51-1, and having the shape of a ball.

The ball joint 5-2 shown in FIG. 5B has the shape of a dumbbell and a lower portion in the shape of a bow, and includes a ball joint lower portion 51-2 having a lower portion inclined downward of both sides thereof, the ball joint intermediate portion 52 provided on the ball joint lower portion 51-2, having a diameter smaller than that of the ball joint lower portion 51-2 and having the shape of a cylinder, and the ball joint upper portion 53 provided on the ball joint intermediate portion 52, having a diameter greater than that of the ball joint intermediate portion 52 and smaller than that of the ball joint lower portion 51-1, and having the shape of a ball.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

The invention claimed is:

1. A denture-fixing attachment freely adjustable in angle and position, the denture-fixing attachment comprising:
   a fixture including a fixture groove;
   a rotation guide member installed at a center of the denture-fixing attachment, the rotation guide member comprising a lower portion extending downward to be inserted into and coupled with the fixture groove of the fixture, a lateral side positioned on the lower portion thereof, and an upper groove recessed in a concave half-moon shape positioned at an upper portion of the rotation guide member;
   a ball joint angle restriction cover positioned on the rotation guide member and having a through hole vertically formed through an inner part of the ball joint angle restriction cover; and
   a ball joint disposed to couple with the upper groove of the rotation guide member and positioned inside the ball joint angle restriction cover,
   wherein the ball joint has a shape of a dumbbell and comprises:
   a ball joint lower portion for coupling with the upper groove of the rotation guide member, the ball joint lower portion having a shape of a ball;
   a ball joint intermediate portion installed at an upper portion of the ball joint lower portion, the ball joint intermediate portion having a shape of a cylinder and having a diameter smaller than a diameter of the ball joint lower portion; and
   a ball joint upper portion installed at an upper portion of the ball joint intermediate portion, the ball joint upper portion having a shape of a ball and having a diameter greater than the diameter of the ball joint intermediate portion and smaller than the diameter of the ball joint lower portion.

2. The denture-fixing attachment of claim 1, wherein the rotation guide member comprises a thread disposed at the lateral side thereof.

3. A denture-fixing attachment freely adjustable in angle and position, the denture-fixing attachment comprising:
   a fixture including a fixture groove;
   a rotation guide member installed at a center of the denture-fixing attachment, the rotation guide member comprising a lower portion extending downward to be inserted into and coupled with the fixture groove of the fixture, a lateral side positioned on the lower portion thereof, and an upper groove recessed in a concave half-moon shape positioned at an upper portion of the rotation guide member;
   a ball joint angle restriction cover positioned on the rotation guide member and having a through hole vertically formed through an inner part of the ball joint angle restriction cover; and
   a ball joint disposed to couple with the upper groove of the rotation guide member and positioned inside the ball joint angle restriction cover,
   wherein the ball joint has a shape of a dumbbell and comprises:
   a ball joint lower portion for coupling with the upper groove of the rotation guide member, the ball joint lower portion having a spherical sector shape with a cone angle of less than 180 degrees;
   a ball joint intermediate portion installed at an upper portion of the ball joint lower portion, the ball joint intermediate portion having a shape of a cylinder and having a diameter smaller than a diameter of the ball joint lower portion; and
   a ball joint upper portion installed at an upper portion of the ball joint intermediate portion, the ball joint upper portion having a shape of a ball and having a diameter greater than the diameter of the ball joint intermediate portion and smaller than the diameter of the ball joint lower portion.

4. A denture-fixing attachment freely adjustable in angle and position, the denture-fixing attachment comprising:
   a fixture including a fixture groove;
   a rotation guide member installed at a center of the denture-fixing attachment, the rotation guide member comprising a lower portion extending downward to be inserted into and coupled with the fixture groove of the fixture, a lateral side positioned on the lower portion thereof, and an upper protrusion protruding in a convex half-moon shape positioned at an upper portion of the rotation guide member;
   a ball joint angle restriction cover positioned on the rotation guide member and having a through hole vertically formed through an inner part of the ball joint angle restriction cover; and
   a ball joint disposed to couple with the upper protrusion of the rotation guide member and positioned inside the ball joint angle restriction cover,
   wherein the ball joint comprises a ball joint lower portion having a lower portion for coupling with the upper protrusion of the rotation guide member, the ball joint lower portion having a concave recessed groove for receiving the upper protrusion of the rotation guide member.

5. The denture-fixing attachment of claim 4, wherein the ball joint further comprises:
- a ball joint intermediate portion installed at an upper portion of the ball joint lower portion, the ball joint intermediate portion having a shape of a cylinder and a diameter smaller than a diameter of the ball joint lower portion; and
- a ball joint upper portion installed at an upper portion of the ball joint intermediate portion, the ball joint upper portion having a shape of a ball and having a diameter greater than the diameter of the ball joint intermediate portion and smaller than the diameter of the ball joint lower portion.

\* \* \* \* \*